United States Patent [19]

Aldrich Paul E. et al.

[11] 4,251,534

[45] Feb. 17, 1981

[54] ANTIHYPERTENSIVE POLYFLUOROHYDROXYISOPROPYL BICYCLIC AND TRICYCLIC CARBOSTYRILS

[75] Inventors: Aldrich Paul E., Wilmington, Del.; Gilbert H. Berezin, West Chester, Pa.

[73] Assignee: E. I. Du Pont de Nemours and Company, Wilmington, Del.

[21] Appl. No.: 863,269

[22] Filed: Dec. 22, 1977

[51] Int. Cl.$^3$ .................... A61K 31/47; C07D 215/22
[52] U.S. Cl. .................... 424/258; 424/244; 424/248.4; 546/157; 544/101; 544/105; 548/218
[58] Field of Search ............ 260/289 K; 424/244, 424/258; 546/157

[56] References Cited

U.S. PATENT DOCUMENTS

| 3,178,348 | 4/1965 | Bickerton | 546/157 |
| 3,514,459 | 5/1970 | Ritter et al. | 546/157 |
| 4,058,612 | 11/1977 | Neustadt | 424/251 |

FOREIGN PATENT DOCUMENTS 980098  9/1965  France .................... 260/289 K

*Primary Examiner*—Jose Tovar
*Assistant Examiner*—D. B. Springer

[57] ABSTRACT

Polyfluorohydroxyisopropyl bicyclic and tricyclic carbostyrils, such as 2,3-dihydro-7-methyl-9-[2,2,2-trifluoro-1-hydroxy-1-(trifluoromethyl)ethyl]-5H-pyrido[1,2,3-de]-1,4-benzoxazin-5-one, useful as antihypertensive agents.

21 Claims, No Drawings

ANTIHYPERTENSIVE POLYFLUOROHYDROXYISOPROPYL BICYCLIC AND TRICYCLIC CARBOSTYRILS

BACKGROUND OF THE INVENTION

This invention relates to polyfluorohydroxyisopropyl bicyclic and tricyclic carbostyril antihypertensives.

Allied Chemical Corporation, in British Pat. No. 1,029,048, discloses hexahalohydroxyisopropyl aryl derivatives as intermediates in the preparation of automatic carboxylic acids.

Jones, E. S., in U.S. Pat. Nos. 3,405,177 and 3,541,152, discloses hexahalohydroxyisopropyl aromatic amines useful as intermediates in the preparation of azo dyestuffs, polyesters, polyamides, insecticides, plasticizers and pharmaceuticals.

Gilbert, E. E., in U.S. Pat. No. 3,532,753, discloses aromatic amino derivatives of hexahaloacetone useful as insecticides.

German OS 2,552,993 discloses compounds containing a ureido or isoureido function which have utility as antihypertensive agents.

Myer, H., et al., in U.S. Pat. No. 3,907,807, discloses benzoquinolizine antihypertensive agents; the following compound is exemplary:

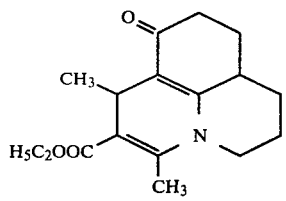

Many current antihypertensive agents produce unwanted side effects because of their undesirable mechanism of action. For example, guanethidine is an adrenergic neurone blocker, mecamylamine is a ganglion blocker, phenoxybenzamine is an α-adrenergic receptor blocker, and reserpine is a catecholamine depletor. Each of these mechanisms of action is undesirable because of the serious side effects produced. The compounds of this invention appear to lower blood pressure by a desirable mechanism of action—direct peripheral vasodilation—and, therefore have a distinct advantage over the above undesirable acting antihypertensive agents.

Furthermore, these compounds do not appear to produce central nervous system effects such as those seen with clonidine and α-methyldopa administration.

SUMMARY OF THE INVENTION

According to this invention there is provided compounds of the following formula, processes for their manufacture, pharmaceutical compositions containing them, and methods of using them to treat hypertension in mammals.

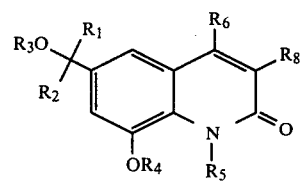

where
- $R_1$ = $CF_3$ or $CF_2H$;
- $R_2$ = $CF_3$, $CF_2H$ or $CF_2Cl$;
- $R_3$ = H, acyl or alkyl of 1–6 carbon atoms;
- $R_4$ = methyl, ethyl, allyl or propyl;
- $R_5$ = hydrogen, methyl or ethyl; or
- $R_4$ and $R_5$ taken together =

$$-\underset{R_7}{CH}-, \quad -\underset{R_7}{CHCH_2}-, \quad -CH_2CH_2CH_2- \text{ or } -\underset{CH_2OH}{CH}-CH_2-;$$

provided the —$CH_2OH$ moiety is attached to the carbon atom directly attached to the nitrogen atom;
- $R_7$ = H, methyl or ethyl;
- $R_6$ = methyl or ethyl; and
- $R_8$ = hydrogen or methyl; and pharmaceutically suitable salts provided $R_3$ = hydrogen.

DETAILED DESCRIPTION OF THE INVENTION

Preferred for their high degree of activity are those compounds of Formula (1) where, independently:
- (a) $R_3$ = hydrogen; or
- (b) $R_4$ = methyl and $R_5$ = H; or
- (c) $R_4$ and $R_5$ taken together, =

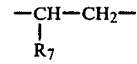

or —$CH_2$—$CH_2$—$CH_2$—, where $R_7$ = hydrogen, methyl or ethyl; or
- (d) $R_8$ = hydrogen.

Where $R_3$ is alkyl, a preferred definition is alkyl of 1–4 carbon atoms and more preferably 1–2 carbon atoms.

The following compounds are specifically preferred:
- (a) 8-methoxy-4-methyl-6-[2,2,2-trifluoro-1-hydroxy-1-(trifluoromethyl)ethyl]-2(1H)-quinolinone;
- (b) 2,3-dihydro-7-methyl-9-[2,2,2-trifluoro-1-hydroxy-1-(trifluoromethyl)ethyl]-5H-pyrido[1,2,3-de]-1,4-benzoxazin-5-one; and
- (c) 2,3-dihydro-3,7-dimethyl-9-[2,2,2-trifluoro-1-hydroxy-1-(trifluoromethyl)ethyl]-5H-pyrido[1,2,3-de]-1,4-benzoxazin-5-one.

Acyl Derivatives

Acyl derivatives of the hydroxy function of the compounds of this invention show excellent antihypertensive activity. The acyl derivatives (i.e., where $R_3$ is not hydrogen or alkyl) are hydrolyzed easily to the parent hydroxy compound ($R_3$=H), and it is believed that their antihypertensive effect is due to a facile in vivo hydrolysis. Acylation can be used to give derivatives with a variety of different physical properties, but with little difference in biological properties from the parent hydroxy compound. It is concluded, therefore, that the range of acyl groups is practically unlimited and not critical for antihypertensive activity. Among the acyl groups that can be used are alkanoyl, alkenoyl and aroyl.

Synthesis

Polyfluorohydroxyisopropyl amine precursors where $R_4$ is methyl or hydrogen, are prepared in the following manner:

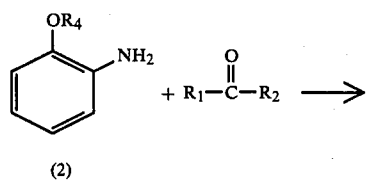

(2)

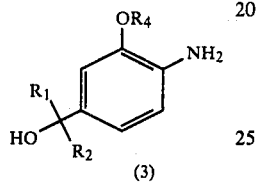

(3)

Compounds of the above type where $R_1=R_2=CF_3$ have been prepared by E. E. Gilbert et al., *J. Org. Chem.* 30, 1001 (1965) and *J. Het. Chem.*, 6, 483 (1969). The procedure described in *J. Het. Chem.* 6, 483 (1969) utilizes the reaction of an aniline with a hydrate of hexafluoroacetone to give an adduct such as (3). This procedure is preferred for most additions of polyfluoroacetones in this series. However, in some cases, it may be preferable to react the aniline with the polyfluoroacetone in the presence of an acidic catalyst such as aluminum chloride.

Precursors in which $R_4$ and $R_5$ are joined together are prepared as described in the following reaction schemes.

1,4-Benzoxazines 1,4-Benzoxazine precursors, unsubstituted in the 2- or 3-position or substituted in the 2-position with a methyl or ethyl group, are prepared as follows:

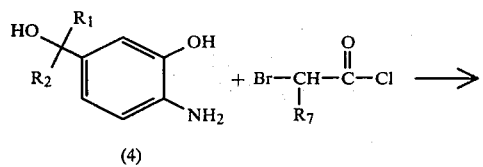

(4)

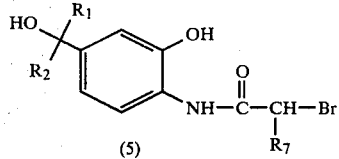

(5)

Reaction of (4) with an alpha-haloacidchloride gives the amide (5). Treatment of (5) with a base in aqueous or alcoholic solution gives the 1,4-benzoxazin-3-one (6). Reduction of (6) with a reducing agent such sodium bis(2-methoxethoxy)aluminum hydride or diborane gives the precursor 1,4-benzoxazine, (7)

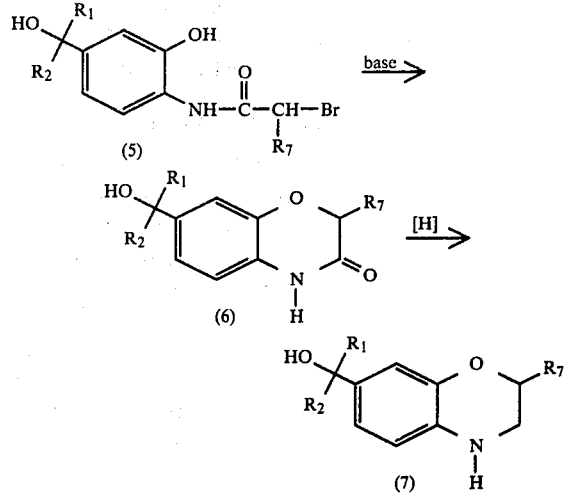

1,4-Benzoxazine precursors substituted with methyl or ethyl in the 3-position are prepared as follows:

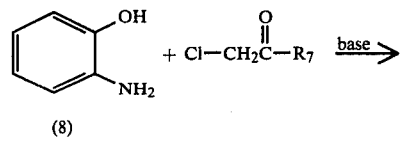

(8)

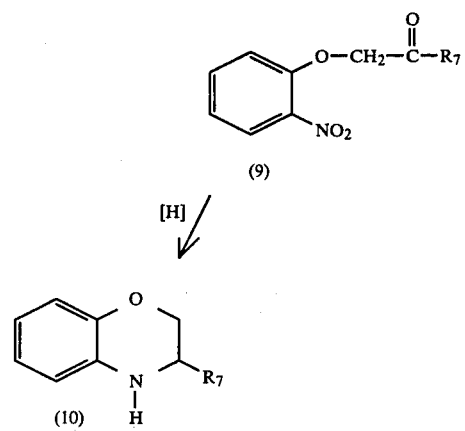

Treatment of nitrophenol (8) with a 1-haloketone in the presence of a base such as sodium ethoxide gives the phenoxyketone (9). Reduction of (9) with hydrogen in the presence of a catalyst, such as 5% palladium or carbon, gives the 1,4-benzoxazine (10). This procedure is described by G. P. Ellis; G. Baker; D. A. Wilson *J. Chem. Soc.*, C(11), 2079-82(1971)

Treatment of (10) with a polyfluoroacetone gives the precursor 1,4-benzoxazine (11).

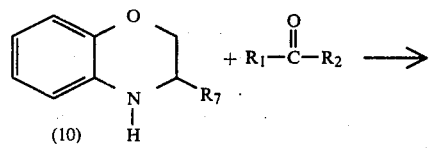

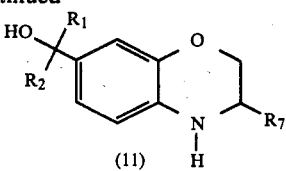

(11)

1,5-Benzoxazepine 1,5-Benzoxazepine is prepared by the procedure of J. Sam et al., *J. Pharm. Sci.*, 60 (9), 1370 (1971).

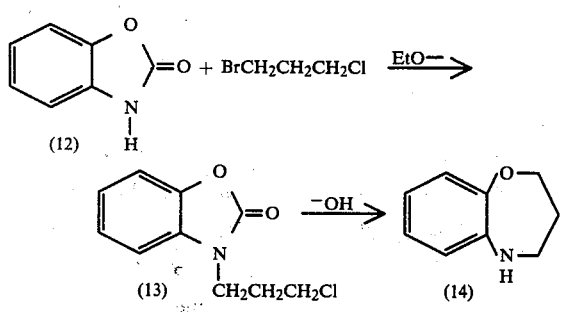

2-Benzoxazolinone (12) is treated with bromochloropropane and sodium ethoxide in ethanol to give (13). The reaction of (13) with ethanolic potassium hydroxide gives (14). Polyfluoroacetones react with (14) to give the precursor (15).

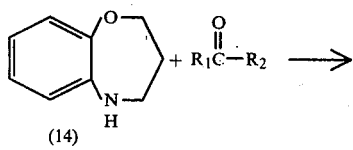

(14)

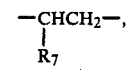

(15)

Intermediate amides

Intermediate amides (17) are prepared as shown in the following reaction:

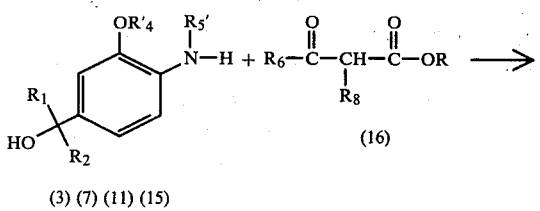

(3) (7) (11) (15)

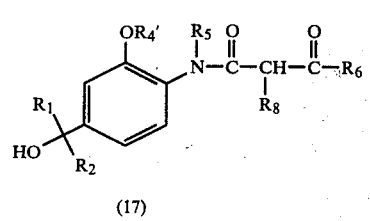

(17)

where $R_1$, $R_2$, $R_4$, $R_5$, $R_6$ and $R_8$ are as previously defined;

$R'_4$ = methyl;
$R'_5$ = hydrogen; or
$R'_4$ and $R'_5$ taken together =

$$-\underset{\underset{R_7}{|}}{C}HCH_2-,$$

or $-CH_2CH_2CH_2-$; and

R is an alkyl group of 1-5 carbon atoms.

The amide (17) is prepared by heating equimolar amounts of amine (3), (7), (11) or (15) and ketoester (16) in an oil bath. The preferred temperature range is about 180°-220° C. Alternatively, the reactants can be refluxed together in a high-boiling solvent, for example, xylene.

The reaction can be conveniently followed by periodically removing a test portion and performing thin layer chromatography. When no further reaction is observed, the amide (17) is isolated by crystallization and/or chromatography. Occasionally, purification is difficult and, therefore, cyclization of the crude amide is more convenient.

When $R_8$=H and $R_6$=CH$_3$, the amide (17) is prepared more conveniently and in better yield using diketene instead of the ketoester (16). A slight excess of diketene is added to the amine (3), (7), (11) or (15) dissolved in an inert solvent (for example, anhydrous tetrahydrofuran or toluene), held at room temperature. If the reaction is slow (as indicated by thin layer chromatography), the mixture is heated until no further reaction is observed. The crude product is often satisfactory to be used directly for cyclization, but it can be purified by recrystallization and/or chromatography.

The cyclization products are prepared as shown in the following reaction:

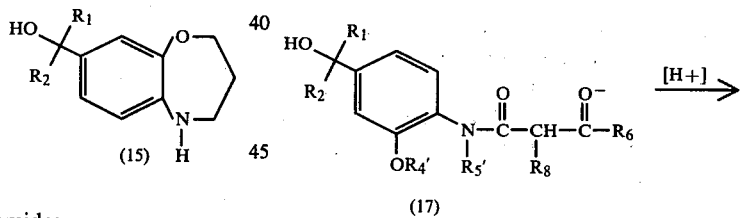

(17)

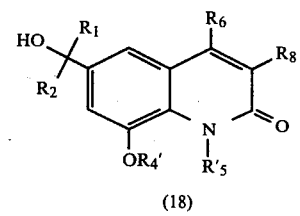

(18)

Cyclization is accomplished by heating the amide (17) in a condensing agent such as sulfuric aid or polyphosphoric acid. Usually, heating in concentrated sulfuric acid for one to two days at 50°-70° C. completes the reaction. Completion of the reaction can be conveniently checked by removing a small test sample, isolating the solids, and analyzing by thin layer chromatography. The product (18) is isolated by pouring the acid solution into excess ice water, removing the precipitated material by filtration, washing and drying. Further purification, if necessary, can be done by recrystallization and/or chromatography.

The compounds of formula (1) where $R_4$=methyl and $R_5$=methyl or ethyl can be prepared by cyclization of the amide (17) where $R'_4$ is methyl and $R'_5$ is hydrogen. The product (18′) [$R'_4$ methyl and $R'_5$=hydrogen] is then treated with $R'_3X$ ($R'_3$=alkyl of 1–6 carbons or

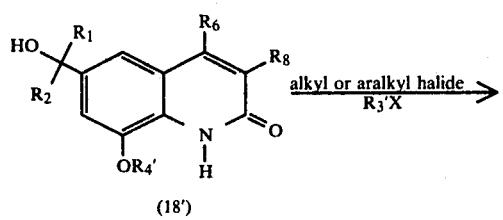

where $R_{10}$=H, F, Cl, Br, $NO_2$, phenyl or $CH_3-$, X=halogen), an alkyl halide such as methyl iodide or aralkyl halide such as benzyl bromide, in a solvent such as dimethylformamide with a base such as potassium carbonate, or sodium hydride, to give the alkylated compound (19)

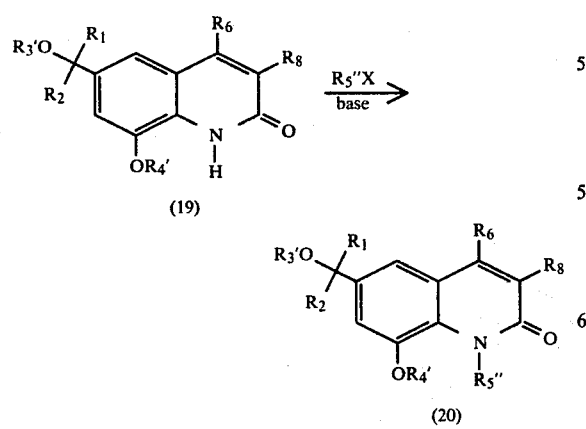

The compound (19) may then be alkylated on nitrogen by use of a base such as potassium carbonate, sodium hydride, or thallium ethoxide in a solvent such as dimethylformamide with an alkyl halide or sulfate $R''_5X$, ($R''_5$=—$CH_3$ or —$CH_2CH_3$, X=halogen or sulfate) to give (20)

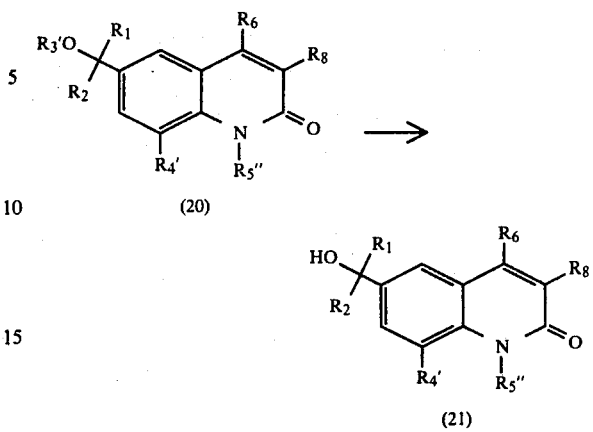

The aralkyl group $R'_3$ on compound (20) may be removed by hydrogenolysis to give compound (21) where $R'_4$ and $R'_5$ are alkyl, Compounds of the type represented by (18′) where $R_1$, $R_2$, $R_6$ and $R_8$ are as defined for (1) and $R'_4$ is methyl may be used to prepare two series of compounds as follows:

8-Alkoxyquinolinones

The treatment of (18′) with 48% hydrogen bromide solution or pyridine hydrochloride gives (22) where $R_1$, $R_2$, $R_6$, and $R_8$ are as defined for (1).

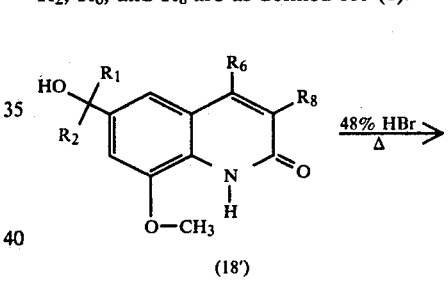

Alkylation of (22) with an alkyl halide such as ethyl iodide, propyl bromide or 1-bromo-2-propene by the use of a base such as potassium carbonate in a solvent such as dimethylformamide gives (23) where $R_1$, $R_2$, $R_3$, $R_5$, $R_6$, and $R_8$ are as previously defined and $R_4$ is ethyl, propyl or allyl.

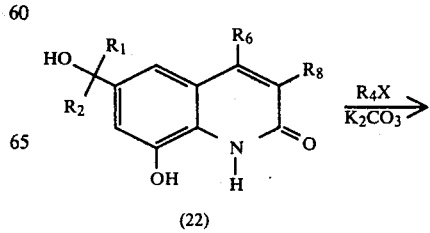

-continued

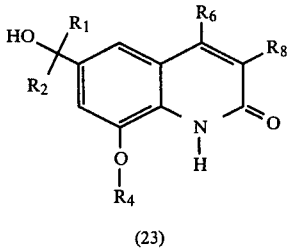

(23)

Oxazolo[5,4,3-ij]quinolin-4-ones

Alkylation of (22) where $R_1$, $R_2$, $R_6$ and $R_8$ are previously defined with dibromomethane, 1,1-dibromoethane or 1,1-dibromopropane by use of a base such as potassium carbonate in a solvent asuch as dimethylformamide gives (24) where $R_1$, $R_2$, and $R_3$ are as previously defined and $R_7$ is H, methyl or ethyl

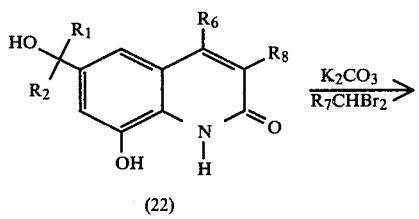

Hydroxymethyl-5H-pyrido[1,2,3-de]-1,4-benzoxazin-5-one

Alkylation of (22) where $R_1$, $R_2$, $R_6$ and $R_8$ are as previously defined with epichlorohydrin gives (25).

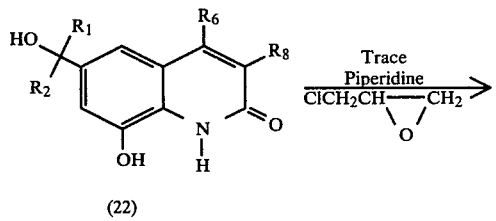

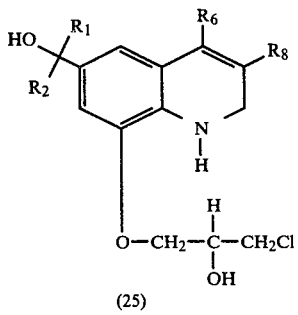

Treatment of (25) with ethanolic sodium hydroxide or potassium hydroxide gives (26)

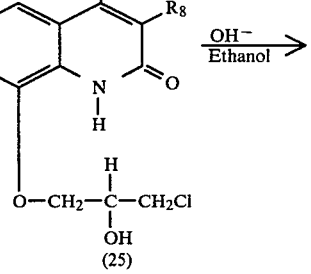

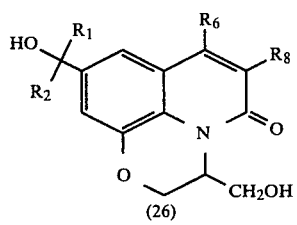

Esters (where $R_3$=acyl) are prepared from (18) by reaction with acid chlorides or anhydrides with or without solvents. Because of the tertiary nature and high acidity of the alcohol group, esterification is rather slow at room temperature but can be greatly accelerated by using high boiling solvents (with or without the addition of a base) or using refluxing pyridine as a solvent and base.

Ethers are prepared from (18) by converting it to a salt by treating with a suitable base (for example, potassium tert-butoxide), then O-alkylating the salt by heating with a dialkyl sulfate or alkyl halide.

To further illustrate the present invention, the following examples are provided. All parts are by weight and temperatures in degrees centigrade unless otherwise specified.

EXAMPLE 1

4-Amino-3-hydroxy[2,2,2-trifluoro-1-hydroxy-1-(trifluoromethyl)ethyl]-benzene

To 390 gm. (2 moles) of hexafluoroacetone sesquihydrate is added 109 gm. (1 mole) of 2-aminohydroxybenzene. The mixture is stirred and heated at reflux in a nitrogen atmosphere for 24 hours. At the end of this period, the solution is concentrated and the residual material is added to 2 liters of water. The aqueous mixture is extracted with ether. The ethereal layer is dried over anhydrous magnesium sulfate and filtered. The filtrate is concentrated to give an oily solid. The oily solid is purified by chromatography on silica gel. Elution with 75% toluene/25% ethyl acetate gives a solid. The solid is recrystallized from ethyl acetate/hexane to give 58 gm of 4-amino-3-hydroxy[2,2,2-trifluoro-1-hydroxy-1-(trifluoromethyl)ethyl]-benzene (m.p. 168°–170°).

EXAMPLES 2-3

The procedure of Example 1 may be used with the appropriate fluoroketone and 2-amino-hydroxybenzene to obtain the indicated product.

| Exam. No. | Flouroketone | Product |
|---|---|---|
| 2. | CF$_2$H—C(=O)—CF$_3$ | HO, CHF$_2$, CF$_3$ substituted benzene with OH and NH$_2$ |
| 3. | CF$_2$Cl—C(=O)—CF$_3$ | HO, CF$_2$Cl, CF$_3$ substituted benzene with OH and NH$_2$ |
| 6. | CF$_2$H—C(=O)—CF$_3$ | HO, CHF$_2$, CF$_3$ substituted benzene with OCH$_3$ and NH$_2$ |
| 7. | CF$_2$Cl—C(=O)—CF$_3$ | HO, CF$_2$Cl, CF$_3$ substituted benzene with OCH$_3$ and NH$_2$ |

EXAMPLE 4

4-Amino-[2,2-difluoro-1-hydroxy-1-(difluoro-methyl)ethyl]-3-hydroxybenzene

A mixture of 2-amino-hydroxybenzene, toluene and sym-tetrafluoroacetone can be heated in a Hastelloy ® bomb. The solvent can be removed by evaporation and the residual material can be purified by chromatography on silica gel to give 4-amino[2,2-difluoro-1-hydroxy-1-(difluoromethyl)ethyl]-3-hydroxybenzene.

EXAMPLE 5

4-Amino-3-methoxy-[2,2,2-trifluoro-1-hydroxy-1-(trifluoromethyl)ethyl]benzene

To 250 gm of hexafluoroacetone trihydrate (1.1 mole) is added 123 gm. (1 mole) of 2-amino-methoxybenzene. The solution is stirred and heated at reflux in a nitrogen atmosphere for 24 hours. At the end of this period the solution is cooled. The resulting solid is purified by chromatography; elution with 90% toluene-10% ethyl acetate gives a crystalline solid. The solid is recrystallized from ether/petroleum ether to give 150 gm. 4-amino-3-methoxy[2,2,2-trifluoro-1-hydroxy-1-(trifluoromethyl)ethyl]-benzene m.p. 129°-131°.

EXAMPLES 6–7

The procedure of Example 1 can be used with the appropriate fluoroketone and 2-amino-methoxybenzene to obtain the indicated product.

EXAMPLE 8

4-Amino-[2,2-difluoro-1-hydroxy-1-(difluoromethyl)ethyl]-3-methoxybenzene

The procedure of Example 4 is used with 2-aminomethoxybenzene and sym-tetrafluoroacetone to give 4-amino[2,2-difluoro-1-hydroxy-1-(difluoromethyl)ethyl]-3-methoxybenzene.

EXAMPLE 9

3,4-Dihydro-3-methyl-7-[2,2,2-trifluoro-1-hydroxy-1-(trifluoromethyl)ethyl]-2-H-1,4-benzoxazine To 50 mg. (0.23 mole) of hexafluoroacetone trihydrate is added 30 gm. (0.20 mole) of 3,4-dihydro-3-methyl-2H-1,4-benzoxazine. The mixture is stirred and heated at reflux in a nitrogen atmosphere for 18 hours. At the end of this period the resultant solution is added to 500 ml. of ice water. The aqueous mixture is extracted with ether. The ethereal solution is dried with anhydrous magnesium sulfate. The etheral solution is filtered and concentrated. The residual solid is recrystallized from chlorobutane/hexane to give 30 gm. of 3,4-dihydro-3-methyl-7-[2,2,2-trifluoro-1-hydroxy-1-(trifluoromethyl)ethyl]-2H-1,4-benzoxazine m.p. 141°-142°.

EXAMPLES 10–17

The procedure of Example 9 may be used with the appropriate fluoroketone and amine to give the indicated product

| Exam. No. | Amine | Flouroketone | Product |
|---|---|---|---|
| 10. | 3,4-dihydro-3-methyl-2H-1,4-benzoxazine | HCF$_2$—C(=O)—CF$_3$ | HO, HCF$_2$, CF$_3$ substituted benzoxazine |
| 11. | 3,4-dihydro-3-methyl-2H-1,4-benzoxazine | ClCF$_2$—C(=O)—CF$_3$ | HO, ClCF$_2$, CF$_3$ substituted benzoxazine |
| 12. | 3,4-dihydro-3-ethyl-2H-1,4-benzoxazine | CF$_3$—C(=O)—CF$_3$ | HO, CF$_3$, CF$_3$ substituted benzoxazine with C$_2$H$_5$ |

-continued

| Exam. No. | Amine | Flouroketone | Product |
|---|---|---|---|
| 13. | 2-(2-aminophenoxy)-N-ethyl (ortho-NH, C2H5) benzomorpholine type | HCF2—C(=O)—CF3 | HO-C(HCF2)(CF3)-aryl-O-CH2-CH(C2H5)-NH- |
| 14. | same amine as 13 | ClCF2—C(=O)—CF3 | HO-C(ClCF2)(CF3)-aryl product |
| 15. | 2,3,4,5-tetrahydro-1,5-benzoxazepine | CF3—C(=O)—CF3 | HO-C(CF3)2-aryl benzoxazepine; m.p. 120°–121° |
| 16. | same as 15 | HCF2—C(=O)—CF3 | HO-C(HCF2)(CF3)-aryl benzoxazepine |
| 17. | same as 15 | ClCF2—C(=O)—CF3 | HO-C(ClCF2)(CF3)-aryl benzoxazepine |

EXAMPLE 18–20

The procedure of Example 4 can be used with sym-tetrafluoroacetone and the indicated amine to give the indicated product.

EXAMPLE 21

2-Chloro-N-{2-hydroxy-4-[2,2,2-trifluoro-1-hydroxy-1-(trifluoromethyl)ethyl]phenyl}-acetamide To a solution of 55 gm. (0.20 mole) of 4-amino-3-hydroxy[2,2,2-trifluoro-1-hydroxy-1-(trifluoromethyl)ethyl]benzene in 600 ml. toluene stirred and heated to 80° in a nitrogen atmosphere is added dropwise 28 gm.

| Example No. | Amine | Flouroketone | Product |
|---|---|---|---|
| 18. | benzomorpholine with N-H, CH3 substituent | HF2C—C(=O)—CF2H | HO-C(HCF2)2-aryl product, CH3 |
| 19. | benzomorpholine with N-H, C2H5 substituent | HF2C—C(=O)—CF2H | HO-C(HCF2)2-aryl product, C2H5 |
| 20. | 2,3,4,5-tetrahydro-1,5-benzoxazepine | HF2C—C(=O)—CF2H | HO-C(HCF2)2-aryl benzoxazepine |

(0.22 mole) of chloro acetyl chloride. When the chloro acetyl chloride has been added, the solution is heated to reflux until analysis by thin layer chromatography indicates the reaction is complete. The solution is cooled and the solid precipitate is filtered and recrystallized from ethylacetate/hexane to give 60 gm. of 2-chloro-N-{2-hydroxy-4-[2,2,2-trifluoro-1-hydroxy-1-(trifluoromethyl)ethyl]phenyl}-acetamide, m.p. 218°-19°.

EXAMPLE 22-26

The procedure of Example 21 can be used with the indicated haloacyl halide and substituted 2-aminohydroxybenzene to give the indicated product.

To a solution of 40 gm. sodium hydroxide (0.30 mole) in 750 ml water is added 53 gm. (0.15 mole) of 2-chloro-N-2-{hydroxy-4-[2,2,2-trifluoro-1-hydroxy-1-(trifluoromethyl)ethyl]phenyl}acetamide with stirring. The solution is stirred for thirty minutes, filtered and heated on the steam bath for an additional 30 minutes. At the end of this period the solution is cooled, and made acidic with concentrated hydrochloric acid. The precipitate is filtered, washed with water until neutral and air dried. Recrystallization of the precipitate from ether/petroleum ether gives 46 gm. of 7-[2,2,2-trifluoro-1-hydroxy-1-(trifluoromethyl)ethyl]-2H-1,4-benzoxazin-3(4H)-one, m.p. 224°-225°.

EXAMPLE 27

7-[2,2,2-Trifluoro-1-hydroxy-1-(trifluoromethyl)ethyl]-2H-1,4-benzoxazin-3(4H)-one

EXAMPLE 28-33

The procedure of Example 27 can be used with the appropriate amide to obtain the indicated product.

| Exam. No. | Amide | Product |
|---|---|---|
| 30 | HO-C(CF$_3$)(CF$_3$)-C$_6$H$_3$(OH)-NH-C(H)(OH)-C(=O)-C(Br)(CH$_3$)(H) | HO-C(CF$_3$)(CF$_3$)-benzoxazin-3(4H)-one with CH$_3$ |
| 31 | HO-C(HCF$_2$)(CF$_3$)-C$_6$H$_3$(OH)-NH-C(H)(OH)-C(=O)-C(Br)(CH$_3$)(H) | HO-C(HCF$_2$)(CF$_3$)-benzoxazin-3(4H)-one with CH$_3$ |
| 31a | HO-C(ClCF$_2$)(CF$_3$)-C$_6$H$_3$(OH)-NH-C(H)(OH)-C(=O)-C(Br)(CH$_3$)(H) | HO-C(ClCF$_2$)(CF$_3$)-benzoxazin-3(4H)-one with CH$_3$ |
| 32 | HO-C(CF$_3$)(CF$_3$)-C$_6$H$_3$(OH)-NH-C(H)(OH)-C(=O)-C(Br)(C$_2$H$_5$)(H) | HO-C(CF$_3$)(CF$_3$)-benzoxazin-3(4H)-one with C$_2$H$_5$ |
| 33 | HO-C(HCF$_2$)(CF$_3$)-C$_6$H$_3$(OH)-NH-C(H)(OH)-C(=O)-C(Br)(C$_2$H$_5$)(H) | HO-C(HCF$_2$)(CF$_3$)-benzoxazin-3(4H)-one with C$_2$H$_5$ |

EXAMPLE 34

3,4-Dihydro-7-[2,2,2-trifluoro-1-hydroxy-1-(trifluoromethyl)ethyl]-2H-1,4-benzoxazine To 150 ml. of 1 molar diborane solution in tetrahydrofuran is added a solution of 31.5 gm. (0.10 mole) of 7-[2,2,2-trifluoro-1-hydroxy-1-(trifluoromethyl)ethyl]-2H-1,4-benzoxazin-3(4H)-one in 150 ml. of anhydrous tetrahydrofuran over a 15 minute period. During the addition the temperature of the solution rose to 40°. When the addition is complete the solution is heated to reflux with stirring under nitrogen for 18 hours. At the end of this period the solution is cooled to 0° and concentrated hydrochloric acid is added until the solution is acidic. The solution is concentrated at reduced pressure at less than 30°. The residual oil is treated with 5% sodium bicarbonate solution. The aqueous mixture is extracted with ether. The ethereal layer is dried with anhydrous magnesium sulfate, filtered and evaporated to give a solid. The solid is recrystallized from chlorobutane to give 19.5 gm. of 3,4-dihydro-7[2,2,2-trifluoro-1-hydroxy-1-(trifluoromethyl)ethyl]-2H-1,4-benzoxazine, m.p. 119°-120°.

EXAMPLES 35-42

The procedure of Example 34 can be used with the appropriate 2H-1,4-benzoxazin-3(4H)-one to give the indicated product.

| Ex. No. | 2H-1,4-benzoxazin-3(4H)-one | Product |
|---|---|---|
| 35 | HO-C(HCF$_2$)(CF$_3$)-benzoxazin-3(4H)-one | HO-C(HCF$_2$)(CF$_3$)-3,4-dihydro-2H-1,4-benzoxazine |
| 36 | HO-C(HCF$_2$)(HCF$_2$)-benzoxazin-3(4H)-one | HO-C(HCF$_2$)(HCF$_2$)-3,4-dihydro-2H-1,4-benzoxazine |

-continued

| Ex. No. | 2H-1,4-benzoxazin-3(4H)-one | Product |
|---|---|---|
| 37 | HO-C(ClCF$_2$)(CF$_3$)-C$_6$H$_3$-(O-CH$_2$-C(=O)-NH) (fused) | HO-C(ClCF$_2$)(CF$_3$)-C$_6$H$_3$-(O-CH$_2$-CH$_2$-NH) (fused) |
| 38 | HO-C(CF$_2$)(CF$_3$)-C$_6$H$_3$-(O-CH(CH$_3$)-C(=O)-NH) | HO-C(CF$_3$)(CF$_3$)-C$_6$H$_3$-(O-CH(CH$_3$)-CH$_2$-NH) |
| 39 | HO-C(HCF$_2$)(CF$_3$)-C$_6$H$_3$-(O-CH(CH$_3$)-C(=O)-NH) | HO-C(HCF$_2$)(CF$_3$)-C$_6$H$_3$-(O-CH(CH$_3$)-CH$_2$-NH) |
| 40 | HO-C(HCF$_2$)(CF$_3$)-C$_6$H$_3$-(O-CH(C$_2$H$_5$)-C(=O)-NH) | HO-C(HCF$_2$)(CF$_3$)-C$_6$H$_3$-(O-CH(C$_2$H$_5$)-CH$_2$-NH) |
| 41 | HO-C(HCF$_2$)(CF$_3$)-C$_6$H$_3$-(O-CH(C$_2$H$_5$)-C(=O)-NH) | HO-C(HCF$_2$)(CF$_3$)-C$_6$H$_3$-(O-CH(C$_2$H$_5$)-CH$_2$-NH) |
| 42 | HO-C(ClCF$_2$)(CF$_3$)-C$_6$H$_3$-(O-CH(C$_2$H$_5$)-C(=O)-NH) | HO-C(ClCF$_2$)(CF$_3$)-C$_6$H$_3$-(O-CH(C$_2$H$_5$)-CH$_2$-NH) |

EXAMPLE 43

8-Methoxy-4-methyl-6-[2,2,2-trifluoro-1-hydroxy-1-(trifluoromethyl)ethyl-2(1H)-quinolinone To a solution of 322 gm. (1.20 moles) of 4-amino-3-methoxy-[2,2,2-trifluoro-1-hydroxy-1-(trifluoromethyl)ethyl]-benzene in 1300 ml. toluene stirred in a nitrogen atmosphere is added 106 gm. (1.22 moles) of diketene. The solution is heated at reflux and stirred for 18 hours. At the end of this period the solution is cooled. The precipitate that forms is filtered and recrystallized from 1-chlorobutane to give 275 gm. of N-{2-methoxy-4-[2,2,2-trifluoro-1-hydroxy-1-(trifluoromethyl)ethyl]-phenyl}-3-oxo-butanamide, m.p. 133°–135°.

To 400 ml. of concentrated sulfuric acid is added 200 gm. (0.54 mole) of N-{2-methoxy-4-[2,2,2-trifluoro-1-hydroxy-1-(trifluoromethyl)ethyl]phenyl}-3-oxobutanamide. The solution is heated to 56° with stirring for 72 hours. At the end of this period the solution is added to 2 liters of ice water. The resultant precipitate is filtered and washed with water until the washes are neutral. The residual solid is recrystallized from acetonitrile-ethanol to give 33 gm. of 8-methoxy-4-methyl-6-[2,2,2-trifluoro-1-hydroxy-1-(trifluoromethyl)ethyl]-2-(1H)-quinolinone. If desired the precipitate obtained from the ice water may be purified by chromatography on silicic acid. Elution with 60% toluene/40% ethyl acetate removes impurities. The purified product is obtained by elution with 50% ethyl acetate/50% methanol, m.p. 237°–39°.

EXAMPLES 44–57

The procedure of Example of 43 may be used with the appropriate amine to give the indicated product.

| Ex. No. | Amine | Product |
|---|---|---|
| 44 | HO-C(HCF$_2$)(CF$_3$)- on benzene with NH$_2$ and OCH$_3$ | 6-[C(OH)(HCF$_2$)(CF$_3$)]-4-methyl-8-methoxy-quinolin-2(1H)-one |
| 45 | HO-C(HCF$_2$)(HCF$_2$)- on benzene with NH$_2$ and OCH$_3$ | 6-[C(OH)(HCF$_2$)(HCF$_2$)]-4-methyl-8-methoxy-quinolin-2(1H)-one |
| 46 | HO-C(CF$_3$)(CF$_3$)- on benzoxazine (NH) | corresponding 4-methyl pyrido-benzoxazinone, m.p. 269° C. decomp. |
| 47 | HO-C(HCF$_2$)(CF$_3$)- on benzoxazine (NH) | corresponding 4-methyl pyrido-benzoxazinone |
| 48 | HO-C(ClCF$_2$)(CF$_3$)- on benzoxazine (NH) | corresponding 4-methyl pyrido-benzoxazinone |
| 49 | HO-C(CF$_3$)(CF$_3$)- on 3-methyl-benzoxazine (NH) | corresponding 4-methyl pyrido-(3-methyl)benzoxazinone, m.p. 195–197° C. |
| 50 | HO-C(HCF$_2$)(CF$_3$)- on 3-methyl-benzoxazine (NH) | corresponding 4-methyl pyrido-(3-methyl)benzoxazinone |
| 51 | HO-C(CF$_3$)(CF$_3$)- on 2-methyl-benzoxazine (NH) | corresponding 4-methyl pyrido-(2-methyl)benzoxazinone |
| 52 | HO-C(ClCF$_2$)(CF$_3$)- on 2-methyl-benzoxazine (NH) | corresponding 4-methyl pyrido-(2-methyl)benzoxazinone |

-continued

| Ex. No. | Amine | Product |
|---|---|---|
| 53 | [structure: HO-C(CF3)2-phenyl fused with O-CH2-CH(C2H5)-NH ring] | [structure: corresponding product with CH3-C=CH-C(=O)-N ring] |
| 54 | [structure: HO-C(HCF2)(CF3)-phenyl fused with O-CH2-CH(C2H5)-NH ring] | [structure: corresponding product with CH3-C=CH-C(=O)-N ring] |
| 55 | [structure: HO-C(CF3)2-phenyl fused with O-CH(C2H5)-CH2-NH ring] | [structure: corresponding product with CH3-C=CH-C(=O)-N ring] m.p. 183–184° C. |
| 56 | [structure: HO-C(CF3)2-phenyl fused with 7-membered O-CH2-CH2-CH2-NH ring] | [structure: corresponding product with CH3-C=CH-C(=O)-N ring] |
| 57 | [structure: HO-C(HCF2)(CF3)-phenyl fused with 7-membered O-CH2-CH2-CH2-NH ring] | [structure: corresponding product with CH3-C=CH-C(=O)-N ring] |

EXAMPLE 58

2,3-Dihydro-7-ethyl-9-[2,2,2-trifluoro-1-hydroxy-1-(trifluoromethyl)ethyl]-5H-pyrido[1,2,3-de]-1,4-benzoxazin-5-one.

A stirred mixture of 3,4-dihydro-7-[2,2,2-trifluoro-1-hydroxy-1-(trifluoromethyl)ethyl]-2H-1,4-benzoxazine and ethyl propionylacetate can be heated in an oil bath to give 1-(1,3-dioxopentyl)-3,4-dihydro-7-[2,2,2-trifluoro-1-hydroxy-1-(trifluoromethyl)ethyl]-2H-1,4-benzoxazine.

A stirred mixture of 1-(1,3-dioxopentyl)-3,4-dihydro-7-[2,2,2-trifluoro-1-hydroxy-1-(trifluoromethyl)ethyl]-2H-1,4-benzoxazine and concentrated sulfuric acid can be heated on a steam bath. The solution can be poured into ice water and residual material can be isolated and purified by chromatography to give 2,3-dihydro-7-ethyl-9-[2,2,2-trifluoro-1-hydroxy-1-(trifluoromethyl)ethyl]-5H-pyrido[1,2,3-de]-1,4-benzoxazin-5-one.

EXAMPLES 59–62

The procedure of Example 58 can be used with the appropriate amine to obtain the indicated product.

| Ex. No. | Amine | Product |
|---|---|---|
| 59 | [structure: HO-C(CF3)2-phenyl with NH2 and OCH3 substituents] | [structure: quinolinone product with HO-C(CF3)2, C2H5, OCH3, NH, C=O] |

-continued

| Ex. No. | Amine | Product |
|---|---|---|
| 60 | [structure: HO, HCF2, CF3 substituted aniline with O-CH2-CH2-NH ring] | [structure: quinolinone with HO, HCF2, CF3 and C2H5] |
| 61 | [structure: HO, CF3, CF3 substituted aniline with O-CH2-CH(CH3)-NH ring] | [structure: quinolinone with HO, CF3, CF3 and C2H5, CH3] |
| 62 | [structure: HO, CF3, CF3 substituted aniline with O-CH(C2H5)-CH2-NH ring] | [structure: quinolinone with HO, CF3, CF3 and C2H5, C2H5] |

EXAMPLE 63

8-Hydroxy-4-methyl-6-[2,2,2-trifluoro-1-hydroxy-1-(trifluoromethyl)ethyl]-2(1H)-quinolinone.

To 200 ml. of 48% hydrobromic acid solution is added 40 gm. (0.11 mole) of 8-methoxy-4-methyl-6-[2,2,2-trifluoro-1-hydroxy-1-(trifluoromethyl)ethyl]-2(1H)-quinolinone. The solution is stirred and heated for 48 hours. At the end of this period the solution is diluted with 50 ml. of ice water. The resultant precipitate is filtered, washed with water until neutral and dried.

Recrystallization from acetronitrile-ethanol gives 35 gm. of 8-hydroxy-4-methyl-6-[2,2,2-trifluoro-1-hydroxy-1-(trifluoromethyl)ethyl]-2(1H)-quinolinone, m.p. 277°–79°.

EXAMPLES 64–66

The procedure of Example 63 can be used with the appropriate 2(1H)-quinolinone to obtain the indicated product.

| Ex. No. | 2(1H)-Quinoline | Product |
|---|---|---|
| 64 | [structure: HO, HCF2, CF3, CH3, OCH3 quinolinone] | [structure: HO, HCF2, CF3, CH3, OH quinolinone] |
| 65 | [structure: HO, ClCF2, CF3, CH3, OCH3 quinolinone] | [structure: HO, ClCF2, CF3, CH3, OH quinolinone] |
| 66 | [structure: HO, CF3, CF3, C2H5, OCH3 quinolinone] | [structure: HO, CF3, CF3, C2H5, OH quinolinone] |

EXAMPLE 67

4-Methyl-8-(2-propenyloxy)-6-[2,2,2-trifluoro-1-hydroxy-1-(trifluoromethyl)ethyl]-2(1H)-quinolinone.

To a solution of 6.8 gm. (0.02 mole) of 8-hydroxy-4-methyl-6-[2,2,2-trifluoro-1-hydroxy-1-(trifluoromethyl)ethyl]-2(1H)-quinolinone in 70 ml of dimethyl formamide is added 2.8 gm. (0.02 mole) of potassium carbonate. The solution is stirred for 1 hour. At the end of this period 4.8 gm. (0.04 mole) of 1-bromo-2-propene is added and stirring is continued for an additional two hours. At the end of that period the solution is added to water and the resultant precipitate is filtered. The residual solid is purified by chromatography on silicic acid. Elution with 85% toluene/14% ethyl acetate/1% methanol gives 4 gm. 4-methyl-8-(2-propenyloxy)-6-[2,2,2-trifluoro-1-hydroxy-1-(trifluoromethyl)ethyl]-2(1H)-quinolinone, m.p. 214°–216°.

EXAMPLES 68–70

The procedure of Example 67 can be used with the appropriate 2(1H)-quinolinone and alkyl halide to give the indicated product.

To a solution of 6.8 gm. (0.02 mole) of 8-hydroxy-4-methyl-6-[2,2,2-trifluoro-1-hydroxy-1-(trifluoromethyl)ethyl]-2(1H)-quinolinone is added 2.8 gm. (0.02 mole) of potassium carbonate and 25.3 gm. (0.15 mole) of dibromomethane. The solution is heated and stirred at 70° in a nitrogen atmosphere for 4 hours. At the end of this period the solution is cooled and added to 50 ml. of water. The resultant solid is filtered and purified by chromatography on silicic acid. Elution with 97.5% chloroform/2.5% methanol gives 2.0 gm. of 6-methyl-8-[2,2,2-trifluoro-1-hydroxy-1-(trifluoromethyl)ethyl]-2H,4H-oxazolo[5,4,3-ij]quinolin-4-one, recrystallized from acetonitrile, m.p. 262°–264°.

| Ex. No. | Alkyl Halide | 2(1H)-quinolinone | Product |
|---|---|---|---|
| 68 | $C_3H_7Br$ | (structure) | (structure) m.p. 201–203° |
| 69 | $C_2H_5I$ | (structure) | (structure) |
| 70 | $C_2H_5I$ | (structure) | (structure) |

EXAMPLE 71

6-Methyl-8-[2,2,2-trifluoro-1-hydroxy-1-(trifluoromethyl)ethyl]-2H,4H-oxazolo[5,4,3-ij]quinolin-4-one.

EXAMPLES 72–76

The procedure of Example 71 can be used with the appropriate 2(1H)-quinolinone and 1,1 dihaloalkane to give the indicated product.

| Ex. No. | 2(1H)-quinolinone | 1,1-dihaloalkane | Product |
|---|---|---|---|
| 73 | (structure) | $Br_2CHCH_3$ | (structure) |
| 74 | (structure) | $Br_2CH_2$ | (structure) |

-continued

| Ex. No. | 2(1H)-quinolinone | 1,1-dihaloalkane | Product |
|---|---|---|---|
| 75 | HO-C(HCF2)(CF3)- and 8-OH, 4-CH3 quinolinone | Br2CH2 | cyclized product with O-CH2-O bridge (4-CH3) |
| 76 | HO-C(HCF2)(CF3)- and 8-OH, 4-C2H5 quinolinone | Br2CH2 | cyclized product with O-CH2 bridge (4-C2H5) |

EXAMPLE 77

2,3-Dihydro-3-hydroxymethyl-7-methyl-9-[2,2,2-trifluoro-1-hydroxy-1-(trifluoromethyl)ethyl]-5H-pyrido[1,2,3-de]-1,4-benzoxazin-5-one.

To 60 gm. of epichlorohydrin is added 20 gm. (0.06 mole) of 8-hydroxy-4-methyl-6-[2,2,2-trifluoro-1-hydroxy-1-(trifluoromethyl)ethyl]-2(1H)-quinolinone and four drops of piperidine. The mixture is stirred and heated at 85° for 3 hours. At the end of this period, excess epichlorohydrin is removed by evaporation at reduced pressure. The residual solid is washed with acetonitrile and recrystallized from ethanol to give 16.5 gm. of 8-(3-chloro-2-hydroxypropoxy)-4-methyl-6-[2,2,2-trifluoro-1-hydroxy-1-(trifluoromethyl)ethyl]-2(1H)-quinolinone, m.p. 253°-255°.

To 200 ml. ethanol is added 4.3 gm. (0.01 mole) 8-(3-chloro-2-hydroxypropoxy-4-methyl-6-[2,2,2-trifluoro-1-hydroxy-1-(trifluoromethyl)ethyl]-2(1H)-quinolinone and a solution of 0.5 gm. (0.012 mole) sodium hydroxide in 5 ml. of water. The solution is stirred in a nitrogen atmosphere at room temperature for 20 hours. At the end of this period, the ethanol is removed by evaporation at reduced pressure. The residual solid is washed with water and air dried. The residual solid is recrystalized from toluene and dried under vacuum at 125° to give 3 gm. of 2,3-dihydro-3-hydroxymethyl-7-methyl-9-[2,2,2-trifluoro-1-hydroxy-1-(trifluoromethyl)ethyl]-5H-pyrido[1,2,3-de]-1,4-benzoxazin-5-one, m.p. 177°-179°.

EXAMPLES 78-80

The procedure of Example 77 may be used with appropriate 2(1H)-quinolinone to give the indicated product.

| Ex. No. | 2(1H)-quinolinone | Product |
|---|---|---|
| 78. | HO-C(CF3)2- with 8-OH, 4-C2H5 quinolinone | N-CH2-CH(CH2OH)-O bridged product, 4-C2H5 |
| 79. | HO-C(HCF2)(CF3)- with 8-OH, 4-CH3 quinolinone | N-CH2-CH(CH2OH)-O bridged product, 4-CH3 |
| 80. | HO-C(HCF2)2- with 8-OH, 4-CH3 quinolinone | N-CH2-CH(CH2OH)-O bridged product, 4-CH3 |

EXAMPLE 81

2,3-Dihydro-7-methyl-9-[2,2,2-trifluoro-1-hydroxy-1-(trifluoromethyl)ethyl]-5H-pyrido[1,2,3-de]-1,4-benzoxazin-5-one Propionate.

A stirred suspension of 2,3-dihydro-7-methyl-9-[2,2,2-trifluoro-1-hydroxy-1-(trifluoromethyl)ethyl]-5H-pyrido]1,2,3-de]-1,4-benzoxazin-5-one and propionic anhydride is heated at reflux for 18 hours. At the end of this period the solution is added to water and resulting precipitate is filtered, washed with water, and air dried.

The precipitate is recrystallized to give 2,3-dihydro-7-methyl-9-[2,2,2-trifluoro-1-hydroxy-1-(trifluoromethyl)ethyl]-5H-pyrido[1,2,3-de]-1,4-benzoxazin-5-one propionate.

EXAMPLES 82-85

The procedure of Example 81 can be used with the appropriate bicyclic or tricyclic carbostyril and acid anhydride to give the indicated product.

pyrido[1,2,3-de]-1,4-benzoxazin-5-one in pyridine is added benzoyl chloride. The suspension is stirred and heated at reflux until homogenous. The solution is added to ice cold 2 N hydrochloric acid. The resultant mixture is extracted with ether; the etheral solution is dried with anhydrous magnesium sulfate, filtered and evaporated at reduced pressure to give 2,3-dihydro-7-methyl-9-[2,2,2-trifluoro-1-hydroxy-1-(trifluoromethyl)-ethyl]-5H-pyrido[1,2,3-de]-1,4-benzoxazin-5-one benzoate.

EXAMPLE 86

2,3-Dihydro-7-methyl-9-[2,2,2-trifluoro-1-hydroxy-1-(trifluoromethyl)ethyl]-5H-pyrido[1,2,3-de]-1,4-benzoxazin-5-one benzoate.

To a suspension of 2,3-dihydro-7-methyl-9-[2,2,2-trifluoro-1-hydroxy-1-(trifluoromethyl)ethyl]-5H-

EXAMPLES 87-89

The procedure of Example 86 can be used with the appropriate bicyclic or tricyclic carbostyril and acyl halide to obtain the indicated product.

| Ex. No. | Bicyclic or Tricyclic Carbostyril | Acyl Halide | Product |
|---|---|---|---|
| 88 | [structure: 4-methyl-6-(hexafluoro-2-hydroxyisopropyl)-8-(sec-butoxy)carbostyril] | PhCH₂C(O)Cl | [structure: corresponding phenylacetate ester] |
| 89 | [structure: tricyclic pyrido-benzoxazinone with hexafluorohydroxyisopropyl and 4-methyl] | CH₃—CH=CH—C(O)—Cl | [structure: corresponding crotonate ester] |

EXAMPLE 90

2,3-Dihydro-7-methyl-9-[2,2,2-trifluoro-1-methoxy-1-(trifluoromethyl)ethyl]-5H-pyrido[1,2,3-de]-1,4-benzoxazin-5-one.

to a solution of 2,3-dihydro-7-methyl-9-[2,2,2-trifluoro-1-hydroxy-1-(trifluoromethyl)ethyl]-5H-pyrido[1,2,3-de]-1,4-benzoxazin-5-one in dimethylformamide is added sodium hydride and dimethyl sulfate. The solution is stirred for 24 hours, treated with ethanol and added to water. The resultant recipitate is filtered, triterated with 10% sodium hydroxide solution and filtered. The residual solid is recrystallized to give 2,3-dihydro-7-methyl-9-[2,2,2-trifluoro-1-methoxy-1-(trifluoromethyl) ethyl]-5H-pyrido[1,2,3-de]-1,4-benzoxazin-5-one. If desired sodium hydride may be replaced by a base such as potassium carbonate or potassium t-butoxide and dimethyl sulfate may be replaced by methyl iodide.

EXAMPLES 91–94

The procedure of Example 90 can be used with the appropriate bicyclic or tricyclic carbostyril and alkyl halide or alkyl sulfate to give the indicated product.

| Ex. No. | Bicyclic or Tricyclic Carbostyril | Alkyl Halide or Alkyl Sulfate | Product |
|---|---|---|---|
| 91 | [structure: 4-methyl-6-(hexafluoro-2-hydroxyisopropyl)-8-methoxycarbostyril] | CH₃I | [structure: 8-OCH₃, 6-C(CF₃)₂OCH₃ carbostyril] |
| 92 | [structure: 4-methyl-6-(hexafluoro-2-hydroxyisopropyl)-8-(sec-butoxy)carbostyril] | (CH₃SO₄) | [structure: corresponding methyl ether] |
| 93 | [structure: 4-ethyl-6-[C(CF₃)(CHF₂)OH]-tricyclic benzoxazinone] | (C₂H₅)₂SO₄ | [structure: corresponding ethyl ether with CF₃/CF₃] |
| 94 | [structure: 4-methyl-6-(hexafluoro-2-hydroxyisopropyl) tricyclic pyridobenzoxazinone] | C₂H₅I | [structure: corresponding ethyl ether] |

EXAMPLE 95

8-Methoxy-1,4-dimethyl-6-[2,2,2-trifluoro-1-hydroxy-1-(trifluoromethyl)ethyl]-2(1H)-quinolinone

To a solution of 8-methoxy-4-methyl-6-[2,2,2-trifluoro-1-hydroxy-1-(trifluoromethyl)ethyl]-2(1H)-quinolinone in dimethylformamide is added potassium carbonate and benzyl bromide. The solution is heated with stirring in a nitrogen atmosphere.

When the reaction is complete as indicated by thin layer chromatography, the solvent is removed at reduced pressure and the residual material is treated with water and extracted into ether. The etheral solution is dried with anhydrous magnesium sulfate and filtered. The ether is evaporated at reduced pressure. The residual material is purified by chromatography on silicic acid to give 8-methoxy-4-methyl-6-[2,2,2-trifluoro-1-benzyloxy-1-(trifluoromethyl)ethyl]-2(1H)-quinolinone.

To a solution of 8-methoxy-4-methyl-6-[2,2,2-trifluoro-1-benzyloxy-1-(trifluoromethyl)ethyl]-2(1H)-quinolinone in dimethylformamide is added potassium carbonate and methyl iodide. The solution is stirred and heated until analysis by thin layer chromatography indicates the reaction is complete. The solution is cooled and added to water. The aqueous mixture is extracted with ether. The etheral solution is dried with anhydrous magnesium sulfate, filtered and evaporated at reduced pressure. The residual material is purified by chromatography on silicic acid to give 8-methoxy-1,4-dimethyl-6-[2,2,2-trifluoro-1-benzyloxy-1-(trifluoromethyl)ethyl]-2(1H)-quinolinone.

To a solution of 8-methoxy-1,5-dimethyl-6-[2,2,2-trifluoromethyl)ethyl]-2(1H)-quinolinone in ethanol is added 10% palladium on carbon catalyst. The solution is arranged on a Parr hydrogenation apparatus and shaken with 50 pounds of hydrogen pressure. Shaking is continued until no further hydrogen uptake is noted. The solution is filtered and evaporated to give 8-methoxy-1,4-dimethyl-6-[2,2,2-trifluoro-1-hydroxy-1-(trifluoromethyl)-ethyl]-2(1H)-quinolinone.

Dosage Forms

The compounds of this invention can be administered in the treatment of hypertension according to the invention by any means that effects contact of the active ingredient compound with the site of action in the body of a warm-blooded animal. For example, administration can be parenteral, i.e., subcutaneous, intravenous, intramuscular, or intraperitoneal. Alternatively or concurrently, administration can be by the oral route.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.01 to 50 milligrams per kilogram body weight. Ordinarily, from 0.05 to 40, and preferably 0.1 to 20, milligrams per kilogram per day in one or more applications per day is effective to obtain desired results. For the more potent compounds of the invention, e.g. 8-methoxy-4-methyl-6-[2,2,2-trifluoro-1-hydroxy-1-(trifluoromethyl)ethyl]-2(1H)-quinolinone, the daily dosage ranges are from about 0.02 to 10 mg/kg, preferably 0.1 to 10 kg/mg, and more preferably 0.1 to 5 mg/kg.

Dosage forms (compositions) suitable for internal administration contain from about 0.1 milligrams to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 110 milligrams of lactose, 32 milligrams of talc, and 8 milligrams magnesium stearate.

Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by filtration.

Suspension

An aqueous suspension is prepared for oral administration so that each 5 milliliters contain 10 milligrams of finely divided active ingredient, 500 milligrams of acacia, 5 milligrams of sodium benzoate, 1.0 grams of sorbitol solution, U.S.P., 5 milligrams of sodium saccharin, and 0.025 milliliters of vanilla tincture.

Injectable

A parenteral composition suitable for administration by injection is prepared by dissolving 1% by weight of active ingredient in sodium chloride injection U.S.P. XV and adjusting the pH of the solution to between 6 and 7. The solution is sterilized by filtration.

The antihypertensive activity of the compounds of this invention is evidenced by tests conducted in hypertensive rats. In these tests rats are made hypertensive by subcutaneous implantation of pellets of desoxycorticosterone acetate (DOCA) and by giving the rats saline solution to drink essentially according to the method described by Sturtevant [Annals of Internal Medicine, 49, 1281 (1958)]. Graded dose levels of each compound are administered orally to groups of 8 hypertensive rats. The compound is prepared in an aqueous polyvinyl alcohol/acacia vehicle and administered at a volume to body weight ratio of 5.0 ml/kg. Sixteen hypertensive rats receiving the aqueous vehicle by the same route serve as controls for each test. At various intervals of time after treatment, usually 90 minutes, the systolic arterial blood pressure of each rat is determined by modification of the microphone-manometer technique [Friedman, M. and Freed, S. C., Proc. Soc. Exp. Biol. and Med., 70, 670 (1949)]. That dose of compound which produces a 30 mm mercury (mm Hg) reduction in blood pressure when compared to the mean systolic arterial blood pressure of the control animals is then determined (Effective Dose 30). For example, the indicated ED30's were obtained with the following compounds:

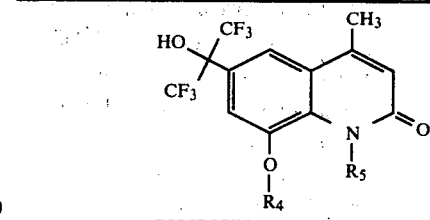

COMPOUND

| $R_4$ | $R_5$ | ED$_{30}$ mg/kg |
|---|---|---|
| CH$_3$ | H | 0.23 |
| —CH$_2$—CH$_2$— | | 0.92 |
| —CH$_2$—CH—<br>        |<br>        CH$_3$ | | 0.46 |
| —CH$_2$— | | 2.8 |
| —CH$_2$CH=CH$_2$ | H | 2.0 |

-continued-

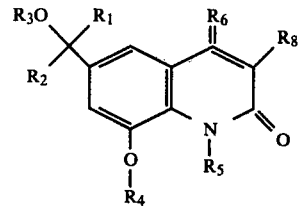

COMPOUND

| $R_4$ | $R_5$ | ED$_{30}$ mg/kg |
|---|---|---|
| —CH$_2$—CH—<br>        |<br>        CH$_2$OH | | 0.45 |
| —CH$_2$—CH$_2$—CH$_2$— | | 0.80 |

"Consisting essentially of" is intended to have its customary meaning: namely, that all specified materials and conditions are very important in practicing the invention but that unspecified materials and conditions are not excluded so long as they do not prevent the benefits of the invention from being realized.

What is claimed is:

1. A compound of the formula

[structure]

where
$R_1$ = CF$_3$ or CF$_2$H;
$R_2$ = CF$_3$, CF$_2$H or CF$_2$Cl;
$R_3$ = hydrogen, alkanoyl, alkenoyl, hydrocarbyl aroyl, or alkyl of 1-6 carbon atoms,
$R_4$ = methyl, ethyl, allyl or propyl;
$R_5$ = hydrogen, methyl or ethyl;
$R_6$ = methyl or ethyl;
$R_8$ = hydrogen or methyl; or a pharmaceutically suitable salt thereof provided $R_3$ = hydrogen.

2. A compound of claim 1 where $R_3$ = hydrogen.

3. A compound of claim 1 where $R_4$ = methyl and $R_5$ = hydrogen.

4. A compound of claim 1 where $R_3$ is alkyl of 1–4 carbon atoms.

5. A compound of claim 4 where $R_3$ is alkyl of 1–2 carbon atoms.

6. A compound of claim 1 where $R_8$ = hydrogen.

7. The compound of claim 1 which is 8-methoxy-4-methyl-6-[2,2,2-trifluoro-1-hydroxy-1-(trifluoromethyl)ethyl]-2(1H)-quinolinone.

8. A pharmaceutical composition consisting essentially of a pharmaceutically suitable carrier and an effective antihypertensive amount of a compound of claim 1.

9. A pharmaceutical composition consisting essentially of a pharmaceutically suitable carrier and an effective antihypertensive amount of a compound of claim 2.

10. A pharmaceutical composition consisting essentially of a pharmaceutically suitable carrier and an effective antihypertensive amount of a compound of claim 3.

11. A pharmaceutical composition consisting essentially of a pharmaceutically suitable carrier and an effective antihypertensive amount of a compound of claim 4.

12. A pharmaceutical composition consisting essentially of a pharmaceutically suitable carrier and an effective antihypertensive amount of a compound of claim 5.

13. A pharmaceutical composition consisting essentially of a pharmaceutically suitable carrier and an effective antihypertensive amount of a compound of claim 6.

14. A pharmaceutical composition consisting essentially of a pharmaceutically suitable carrier and an effective antihypertensive amount of the compound of claim 7.

15. A method of treating hypertension in a mammal which comprises administering to the mammal an effective antihypertensive amount of a compound of claim 1.

16. A method of treating hypertension in a mammal which comprises administering to the mammal an effective antihypertensive amount of a compound of claim 2.

17. A method of treating hypertension in a mammal which comprises administering to the mammal an effective antihypertensive amount of a compound of claim 3.

18. A method of treating hypertension in a mammal which comprises administering to the mammal an effective antihypertensive amount of a compound of claim 4.

19. A method of treating hypertension in a mammal whch comprises administering to the mammal an effective antihypertensive amount of a compound of claim 5.

20. A method of treating hypertension in a mammal which comprises administering to the mammal an effective antihypertensive amount of a compound of claim 6.

21. A method of treating hypertension in a mammal which comprises administering to the mammal an effective antihypertensive amount of the compound of claim 7.

* * * * *